(12) United States Patent
Jen et al.

(10) Patent No.: US 8,771,203 B2
(45) Date of Patent: *Jul. 8, 2014

(54) CATHETER DEPLOYMENT DEVICE

(71) Applicant: Abbott Laboratories, Abbott Park, IL (US)

(72) Inventors: Jimmy Jen, Foster City, CA (US); Robert George, San Jose, CA (US); Jeff Dolin, Belmont, CA (US); Amelia Lasser, Menlo Park, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/025,643

(22) Filed: Sep. 12, 2013

(65) Prior Publication Data
US 2014/0018774 A1  Jan. 16, 2014

Related U.S. Application Data

(63) Continuation of application No. 13/017,553, filed on Jan. 31, 2011, now Pat. No. 8,535,245, which is a continuation of application No. 11/744,087, filed on May 3, 2007, now Pat. No. 7,878,986, which is a continuation of application No. 10/736,459, filed on Dec. 15, 2003, now Pat. No. 7,229,421, which is a continuation of application No. 10/005,981, filed on Dec. 7, 2001, now Pat. No. 6,663,577.

(51) Int. Cl.
*A61B 5/00* (2006.01)
*A61M 25/00* (2006.01)

(52) U.S. Cl.
USPC .................................. 600/585

(58) Field of Classification Search
USPC .......... 600/585; 604/585, 158, 159, 164, 165, 604/171, 264, 164.12, 164.13, 164.09, 604/164.01, 164.02, 164.06, 165.01, 505, 604/22, 28, 30, 31, 95.04; 606/12–15
See application file for complete search history.

(56) References Cited

U.S. PATENT DOCUMENTS

| | | |
|---|---|---|
| 5,656,029 A | 8/1997 | Imran et al. |
| 6,126,649 A | 10/2000 | VanTassel et al. |
| 6,157,852 A | 12/2000 | Selmon et al. |
| 6,217,527 B1 | 4/2001 | Selmon et al. |

(Continued)

FOREIGN PATENT DOCUMENTS

WO    WO03/053504    7/2003

OTHER PUBLICATIONS

U.S. Appl. No. 10/005,981, Mail Date Jul. 29, 2003, Notice of Allowance.

(Continued)

*Primary Examiner* — Brian Szmal
(74) *Attorney, Agent, or Firm* — Workman Nydegger; Jonathan D. Feuchtwang

(57) ABSTRACT

An apparatus for deploying a needle within a lumen is provided. The apparatus includes a housing having a threaded bushing radially disposed therein. The bushing rigidly couples with a nose cone having a guide tip disposed at an end opposite the bushing for penetrating an arterial wall of a lumen. During operation, a user incrementally advances the bushing within the housing, thereby incrementally advancing the guide tip into the lumen. The nose cone also includes a flex guide having a slot configuration which couples with the guide tip which deploys into the lumen along with the guide tip.

24 Claims, 22 Drawing Sheets

(56) References Cited

U.S. PATENT DOCUMENTS

| | | |
|---|---|---|
| 6,544,230 B1 | 4/2003 | Flaherty et al. |
| 6,551,302 B1 | 4/2003 | Rosinko et al. |
| 6,663,577 B2 | 12/2003 | Jen |
| 7,004,173 B2 | 2/2006 | Sparks et al. |
| 7,229,421 B2 | 6/2007 | Jen et al. |
| 7,878,986 B2 | 2/2011 | Jen et al. |
| 8,535,245 B2 | 9/2013 | Jen et al. |

OTHER PUBLICATIONS

U.S. Appl. No. 10/736,459, Mail Date Mar. 31, 2006, Office Action.
U.S. Appl. No. 10/736,459, Mail Date Oct. 25, 2006, Office Action.
U.S. Appl. No. 10/736,459, Mail Date Feb. 5, 2007, Notice of Allowance.
U.S. Appl. No. 10/736,459, Mail Date May 23, 2007, Issue Notification.
U.S. Appl. No. 11/744,087, Mail Date Jun. 26, 2009, Office Action.
U.S. Appl. No. 11/744,087, Mail Date Jan. 5, 2010, Office Action.
U.S. Appl. No. 11/744,087, Mail Date Oct. 1, 2010, Notice of Allowance.
U.S. Appl. No. 13/017,553, Mail Date Nov. 29, 2012, Office Action.
U.S. Appl. No. 13/017,553, Mail Date Jan. 24, 2013, Office Action.
U.S. Appl. No. 13/017,553, Mail Date May 15, 2013, Notice of Allowance.

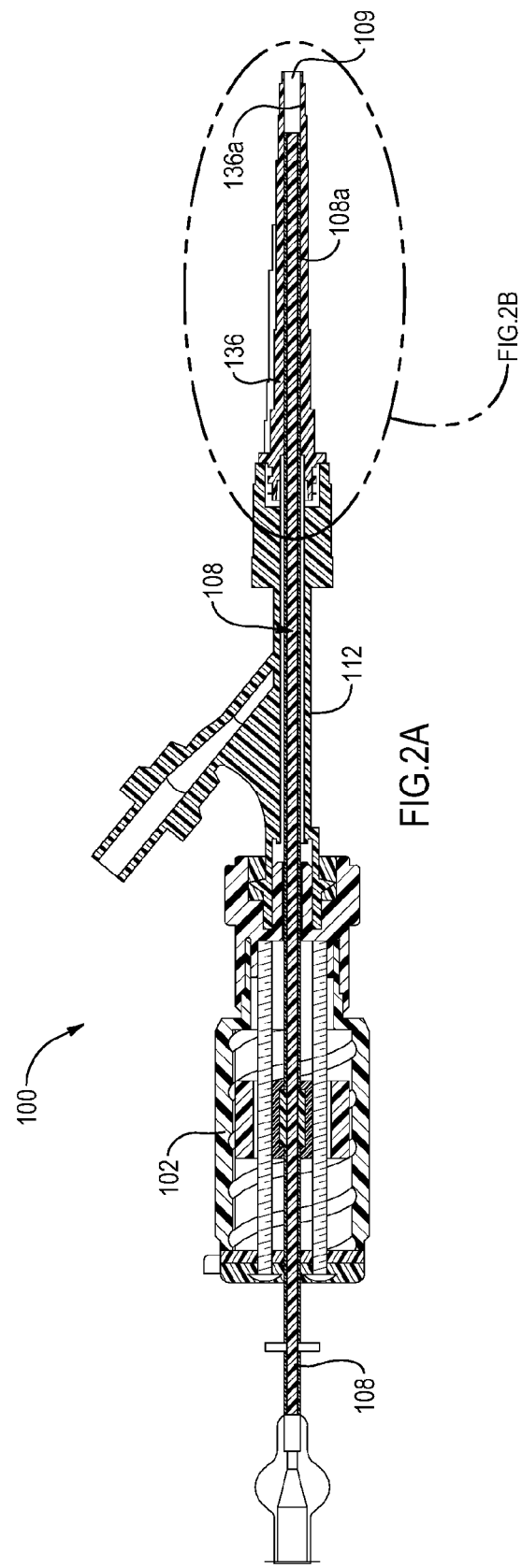

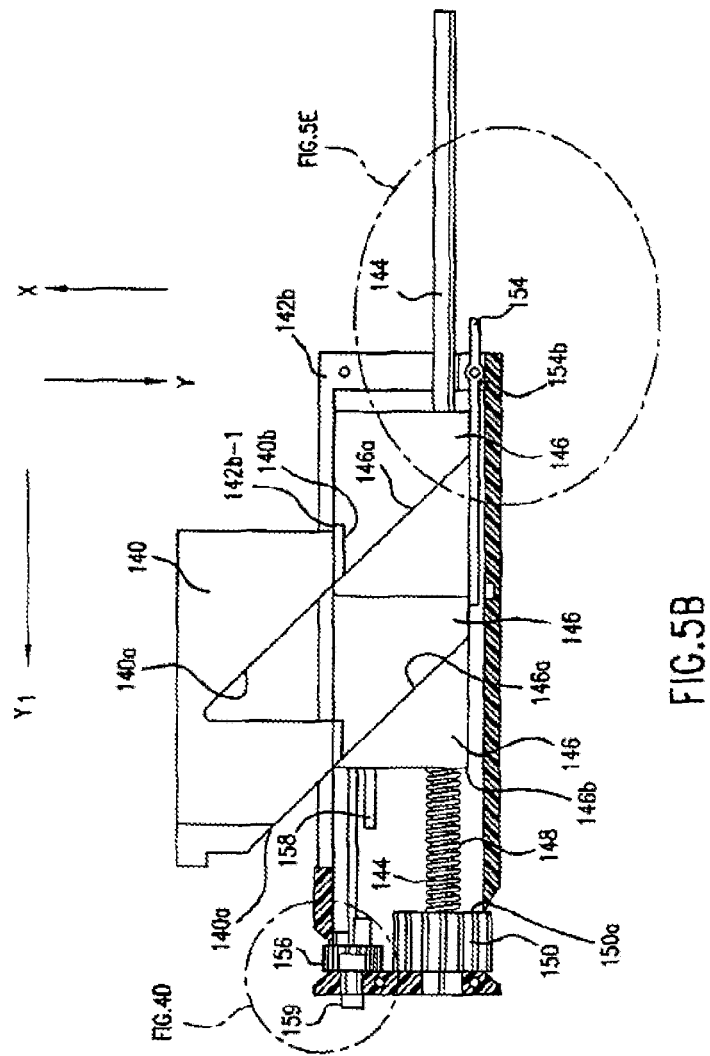

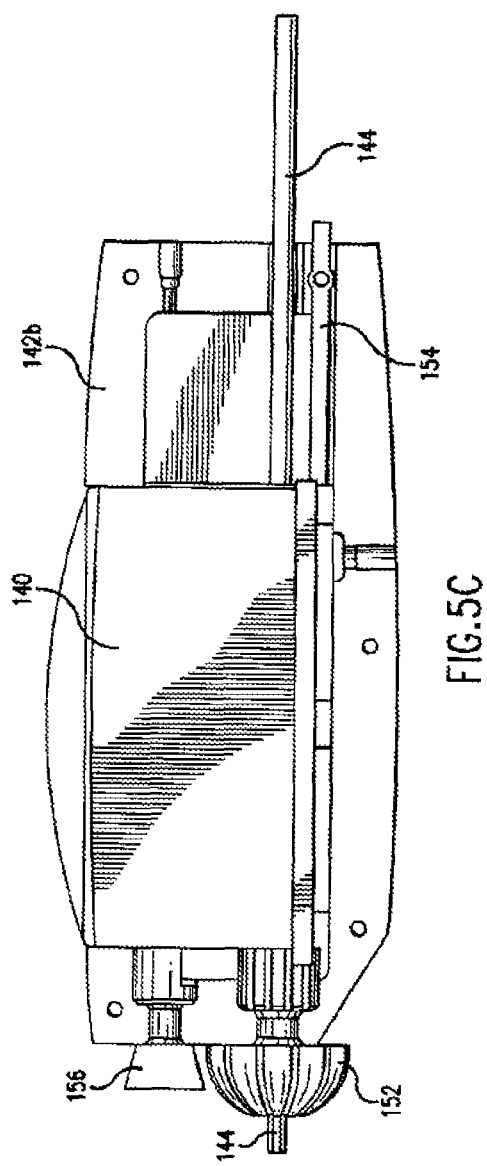

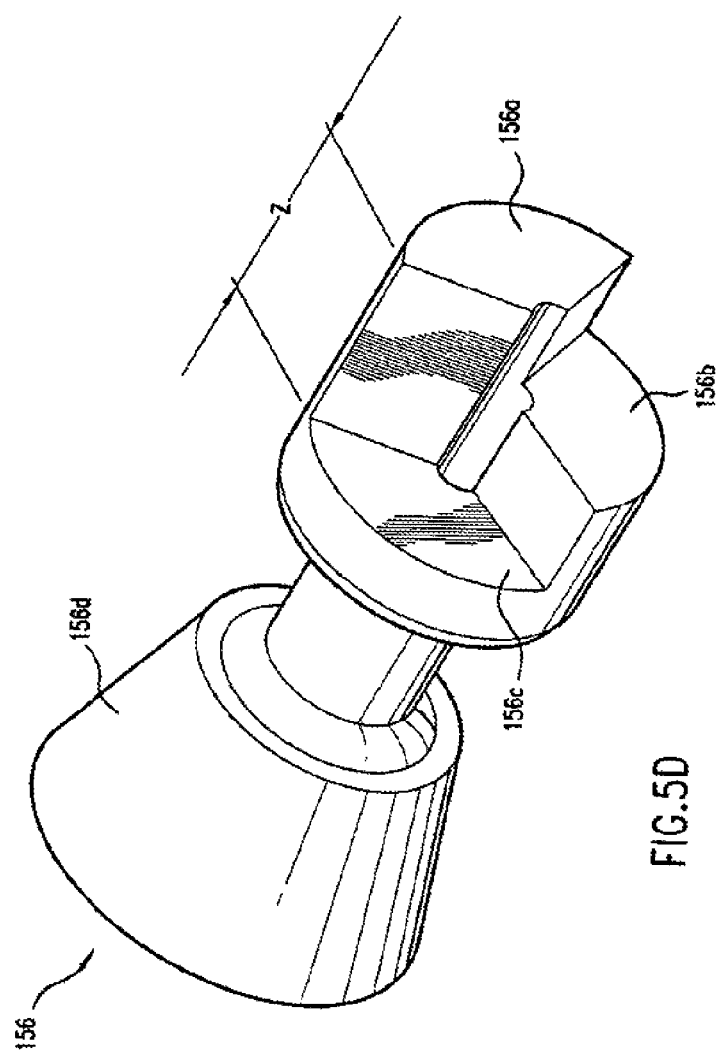

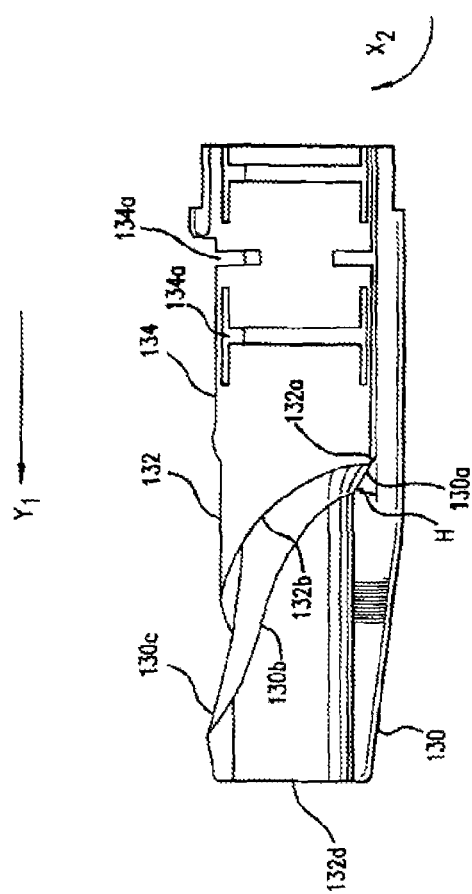

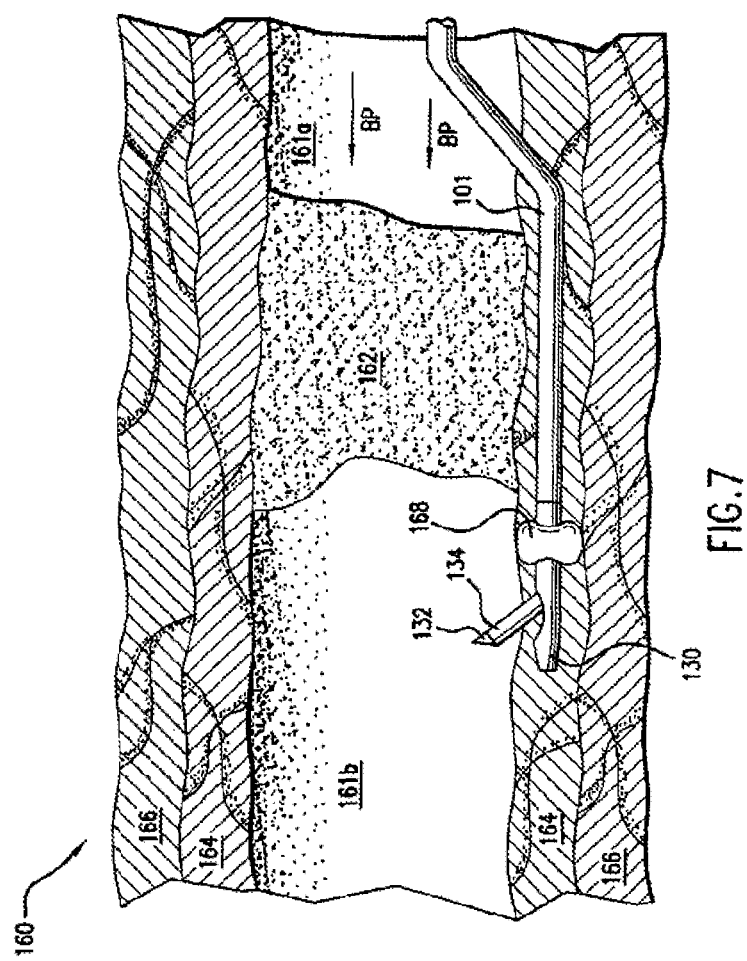

CATHETER DEPLOYMENT DEVICE

CROSS-REFERENCE TO RELATED APPLICATIONS

This application is a continuation of U.S. patent application Ser. No. 13/017,553 filed 31 Jan. 2011, entitled "Catheter Deployment Device", which is a continuation of U.S. patent application Ser. No. 11/744,087 filed 3 May 2007, now U.S. Pat. No. 7,878,986, which is a continuation of U.S. patent application Ser. No. 10/736,459, filed Dec. 15, 2003, entitled "Catheter Deployment Device", now U.S. Pat. No. 7,229,421, which is a continuation of U.S. patent application Ser. No. 10/005,981, filed Dec. 7, 2001, entitled "Catheter Deployment Device", now U.S. Pat. No. 6,663,577, the disclosures of which are each incorporated herein by this reference.

BACKGROUND OF THE INVENTION

1. The Field of the Invention

The present invention relates generally to catheters and more particularly to a device which provides controlled delivery of a guide tip of a catheter within a lumen having chronic total occlusion.

2. The Relevant Technology

Cardiovascular disease is a leading cause of mortality worldwide. Often times, cardiovascular disease occurs upon chronic total occlusion (CTO) of an artery of a patient. CTO typically occurs after a patient develops atherosclerosis. Blockage of an artery may occur in coronary, peripheral or other arteries. As the blockage continues over time, the blockage becomes chronic, thereby leading to CTO.

In order to minimize the potential effects of CTO, passage of blood must be restored to the artery. In the past, attempts to restore blood flow included passing a guidewire through the occlusion, thereby forming a passage through which blood may flow. Nonetheless, while attempting to penetrate the occlusion, the guidewire may inadvertently penetrate a subintimal space between the intimal layer and the adventitial layer of the blood vessel. Once this occurs, redirection of the guidewire back into the blood vessel lumen is nearly impossible. Therefore, the user must pull the guidewire from the subintimal space and start the procedure over thereby increasing the time and overall costs associated with returning blood passage to the artery having CTO.

Moreover, during insertion of the guidewire into the lumen, the configuration of prior art catheter devices allowed for accidental deployment of the guidewire during manipulation of the catheter device. As described in U.S. Pat. No. 6,217,527, the disclosure of which is hereby incorporated by reference, the motion required to deploy a guidewire from a prior art catheter device was the same as the motion for inserting the catheter device into a lumen. To further illustrate, a user introduces a prior art catheter device into the vasculature of a patient using a lateral motion relative to the catheter device. Upon insertion of the catheter device into the arterial lumen, the user deploys the guidewire within the lumen using the same lateral motion relative to the catheter device. As such, during the operation of inserting the catheter device into the lumen, the user may accidentally deploy the guide, thereby potentially damaging the lumen.

In addition to passing a guidewire through the occlusion, past attempts have included forming a subintimal lumen through the subintimal space of the lumen. A user employing this method passes a guidewire between the intima and the adventitia of the lumen. Once the guidewire passes through the subintimal space, the user dissects the subintinal space with an angioplasty balloon and then performs a stenting operation. Upon stenting, an acceptable lumen is formed which bypasses the CTO altogether.

As disclosed in U.S. Pat. No. 6,217,527, a user inserts a guidewire into the subintimal space on one side of the occlusion. Upon insertion of the guidewire, the user inserts a catheter over the guidewire into the subintimal space. The catheter includes a tip configured for penetrating a portion of the arterial wall at a distal side of the occlusion. However, the user must accurately deploy the guide tip within the lumen in order to avoid damaging an arterial wall of the lumen. For example, the user may over deploy the catheter such that the guide tip penetrates the subintimal space, passes through the intended lumen and contacts the arterial wall on the opposite side of the intended lumen, thereby potentially injuring the patient. In addition, prior art guide tips were constructed of flexible material which decreased penetration capabilities of the guide tip through the subintimal space.

Accordingly, a need exists for an automated device which allows precise advancement of a guide tip deployed within a subintimal space of a patient. This new device should include a guide tip resistant to imparted bending forces during penetration of a subintimal space of an arterial wall. The new device should also minimize the possibility of inadvertent deployment of a guide tip during use of the device.

BRIEF SUMMARY OF THE INVENTION

The present invention fills the aforementioned needs by providing a catheter device which incrementally advances a guide tip through a subintimal space of a patient. The present invention also provides a method for incrementally advancing a guide tip through a subintimal space of a patient.

In an embodiment of the present invention, a device for advancing a guide tip through a lumen is disclosed. The device includes a housing having a radial groove, a bushing and an inner key. The bushing is disposed within the housing and operatively couples with the housing via a bushing thread such that the bushing incrementally advances within the housing. The inner key couples with both the bushing at a proximal end of the inner key and a guide tip via a braided shaft at a distal end of the inner key. The guide tip couples with the inner key such that as the bushing incrementally advances within the housing, the guide tip incrementally advances within the lumen. In addition, a flex guide having a slot configuration couples with the guide tip such that the flex guide also deploys into the lumen during use of the catheter device.

BRIEF DESCRIPTION OF THE SEVERAL VIEWS OF THE DRAWINGS

Many advantages of the present invention will be apparent to those skilled in the art with a reading of this specification in conjunction with the attached drawings, wherein like reference numerals are applied to like elements and wherein:

FIG. 2A is a perspective view illustrating an actuator handle of a catheter device in accordance with one embodiment of the present invention.

FIG. 5B is a schematic view of the catheter device shown with respect to FIG. 5A where a left handle of the catheter device has been omitted in accordance with an embodiment of the present invention.

FIG. 5C shows a schematic view of the catheter device shown with reference to FIG. 5A in a deployed position in accordance with an embodiment of the present invention.

FIG. 5D illustrates a perspective view of a stepped hub of the catheter device shown with reference to FIG. 5B in accordance with an embodiment of the present invention.

FIG. 6A is a schematic view of the guide tip shown with reference to FIG. 1 in accordance with an embodiment of the present invention.

FIG. 7 shows a schematic view of an embodiment of the present invention where the catheter device shown with reference to FIG. 2A includes a balloon.

DETAILED DESCRIPTION OF THE INVENTION

A device which provides precise movement of a guide tip within a lumen is disclosed. As an overview, the present invention discloses a device which controls a guide tip through a lumen, such as a blood vessel or an artery, of a patient. The device controls the guide tip while a user, such as a surgeon, crosses an occlusion within an artery of a patient in order to allow blood flow through the artery. The device includes a housing having a guide and bushing disposed within the housing. The configuration of the bushing allows for travel of the bushing along the guide within the housing. In accordance with one embodiment of the present invention, the guide within the housing includes grooves and the configuration of the bushing also includes threads complementary to the grooves in the housing such that the threads in the housing guide the bushing. During use of the device, a user rotates a knob which moves the bushing along the grooves within the housing. As will be discussed in greater detail with respect to the accompanying Figures, when the user advances the bushing within the housing, the bushing advances the guide having a guide tip attached to a distal end thereof, thereby moving the guide tip within the lumen of the patient.

Figure 1:
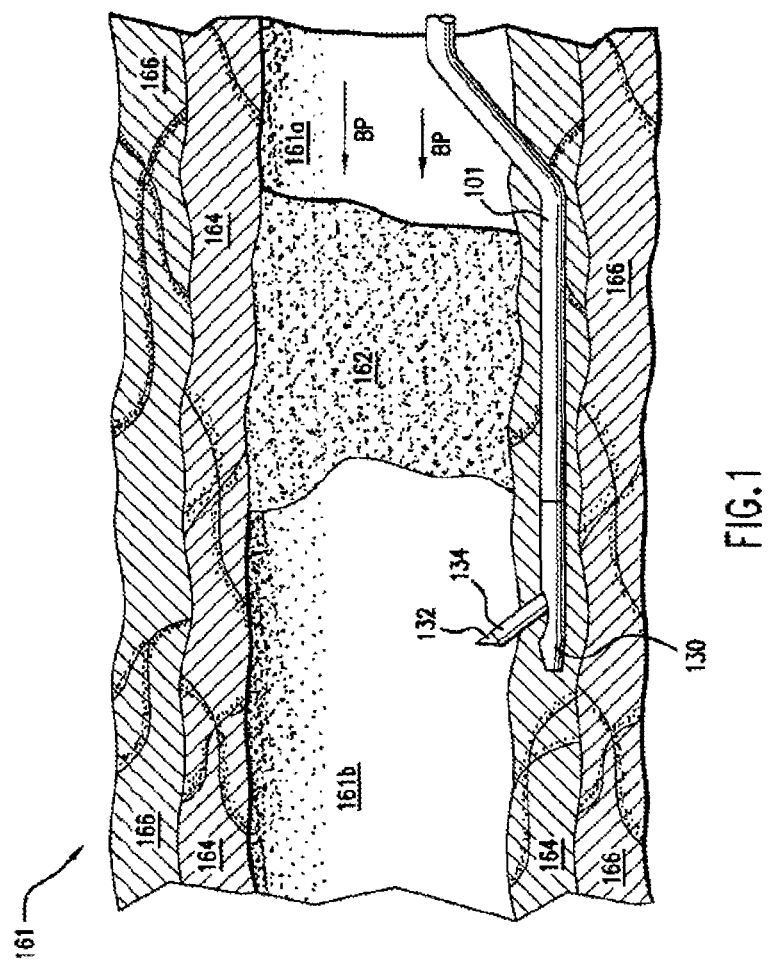
FIG. 1 illustrates a lumen of a patient having an occlusion in accordance with an embodiment of the present invention.

Now making references to the Figures, and more particularly FIG. 1, FIG. 1 illustrates a lumen 161 of a patient having an occlusion 162. As previously described with reference to the background, the occlusion may be caused in any number of ways, including atherosclerosis. As may be seen with reference to FIG. 1, the occlusion 162 prevents blood passage as indicated by directional arrows BP from a side 161a of the occlusion 162 within the lumen 161 to a side 161b of the occlusion 162. Therefore, a user inserts a catheter 101 of a catheter device 100 (shown with reference to FIG. 2A) through the lumen 161 on the side 161a and into a subintimal space defined by an intima layer 164. Upon bypassing the occlusion 162 through the subintimal space 164, a user deploys a flex guide 134 along with a guide tip 132 through the arterial wall and into the lumen 161 on side 161b of the occlusion. The user deploys both the guide tip 132 and the flex guide 134 with the catheter device 100 shown with reference to FIG. 2A.

Figure 6B:
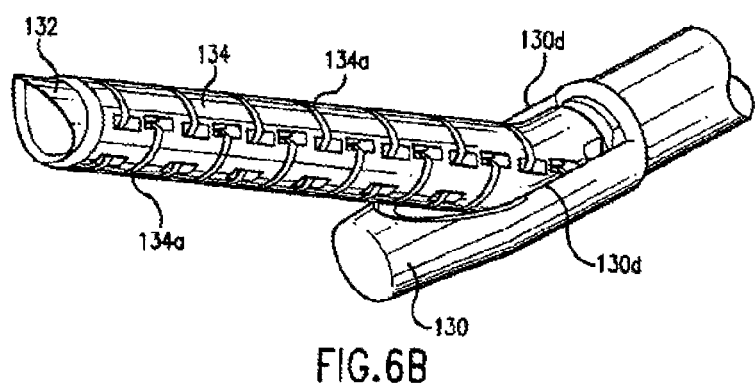
FIG. 6B is a perspective view of the guide tip shown with reference to FIG. 6A where a guide tip and a flex guide are in a deployed position in accordance with an embodiment of the present invention.

FIG. 2A is a perspective view illustrating an actuator handle 102 of the catheter device 100 in accordance with one embodiment of the present invention. The catheter device 100 includes the catheter 101, an inner key 108, a nose cone 130, the guide tip 132 and the flex guide 134 (all shown with reference to FIG. 6A). The inner key 108 includes a braided tube 109 about which the catheter 101 axially disposes. In accordance with one embodiment of the present invention, the catheter 101 may have a length in a range preferably between about 80 cm and about 120 cm and more preferably have a length of about 100 cm. In the preferred embodiment, having a length of 100 cm allows performance of a peripheral vascular intervention procedure using a contralateral approach. In addition, the catheter 101 may also be coated with a hydrophilic coating which provides lubrication for the catheter 101, thereby increasing the ease of operation of the catheter 101 within a patient. Moreover, in this embodiment, the catheter 101 may be constructed from a polyimide and polyurethane tube with braided stainless steel wire. In addition, the catheter 101 encompasses a full length central lumen which is sized to accept a guidewire. In various embodiments of the present invention, the central lumen of the catheter 101 may accept a 0.035 inch or smaller guidewire. In a preferred embodiment of the present invention, the central lumen of the catheter 101 accepts a 0.035 inch guidewire.

The housing 102 and the braided tube 109 couple with the nose cone 130. As such, the braided tube 109 couples the housing 102 with the nose cone 130. In one embodiment of the present invention, the braided tube 109 may be constructed from a stainless steel braided polymide shaft. The catheter device 100 also includes a shaft adapter 136 as more clearly shown with reference to FIG. 2B.

Figure 2B:
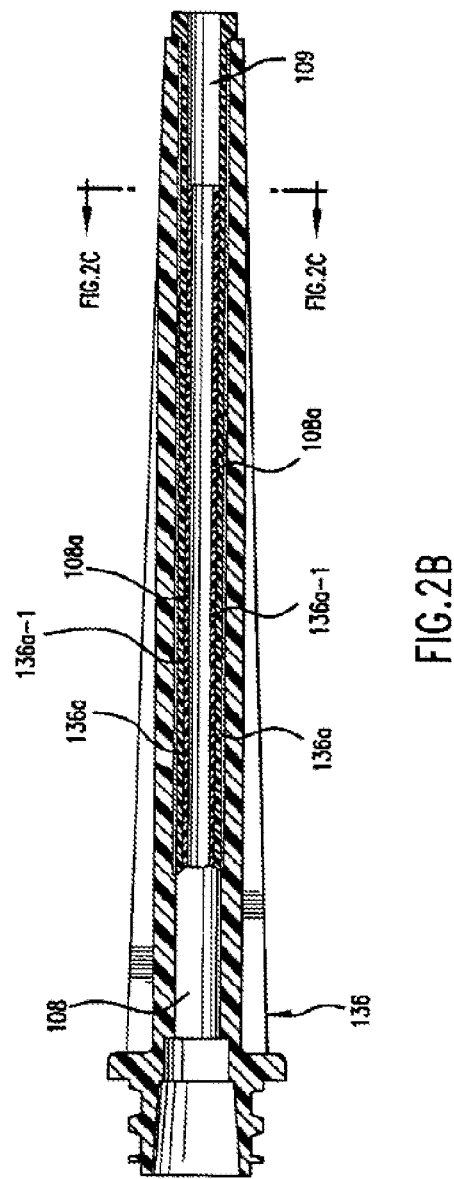
FIG. 2B is an embodiment of the present invention illustrating a schematic view of a shaft adapter of the catheter device shown with respect to FIG. 2A.

FIG. 2B shows an embodiment of the present invention illustrating a schematic view of the shaft adapter 136 of the catheter device 100, shown with respect to FIG. 2A. The shaft adapter 136 maintains a tight tolerance for an inner key 108 and prevents buckling of the braided tube 109 disposed within the inner key 108. In accordance with an embodiment of the present invention, the shaft adapter 136 may be constructed of polycarbonate or any other known plastic. The shaft adapter 136 also includes a guide 136a which steadies the inner key 108 within the catheter device 100 and a lumen of a patient. In accordance with an embodiment of the present invention, a portion of the inner key 108 which extends through the housing 102 and a rotating hemostasis valve 112 has a circular configuration. However, as the inner key 108 enters the guide 136a of the shaft adapter 136a, the configuration of the inner key 108 changes, as shown with respect to FIG. 2C.

Figure 2C:
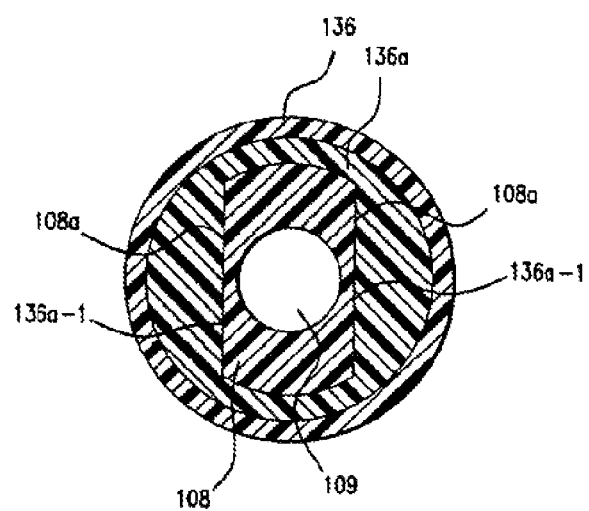
FIG. 2C is a front view of the shaft adapter shown with reference to FIG. 2B in accordance with an embodiment of the present invention.

FIG. 2C is a schematic view of the inner key 108 within the guide 136a and the shaft adapter 136 shown with reference to FIG. 2B in accordance with an embodiment of the present invention. As may be seen with reference to the Figure, the inner key 108 includes surfaces 108a having a planar configuration abutting a surface 136a-1 of the guide 136a. As such, the guide 136a controls rotation of the inner key 108 during use of the catheter device 100, thereby controlling rotation of the guide tip 132 and the braided tube 109. To further illustrate, rotation of the guide 136a rotates the inner key 108 along with the braided tube 109. As the braided tube 109 rotates within the catheter 101, the flex guide 132 also rotates. Therefore, if a user determines that the nose cone 130 (shown with reference to FIG. 6A) must be rotated during procedure, the user rotates the guide 136a, thereby rotating the inner key 108 and the guide tip 132. It should be noted that the inner key 108 may also rotate the guide 136a using the surfaces 108a. Returning attention to FIG. 2A and the catheter device 100, the configuration of the actuator handle 102 allows for precise, incremental advancement of the guide tip 132 within the arterial wall and lumen of a patient, as further described with reference to FIG. 3A.

Figure 3A:
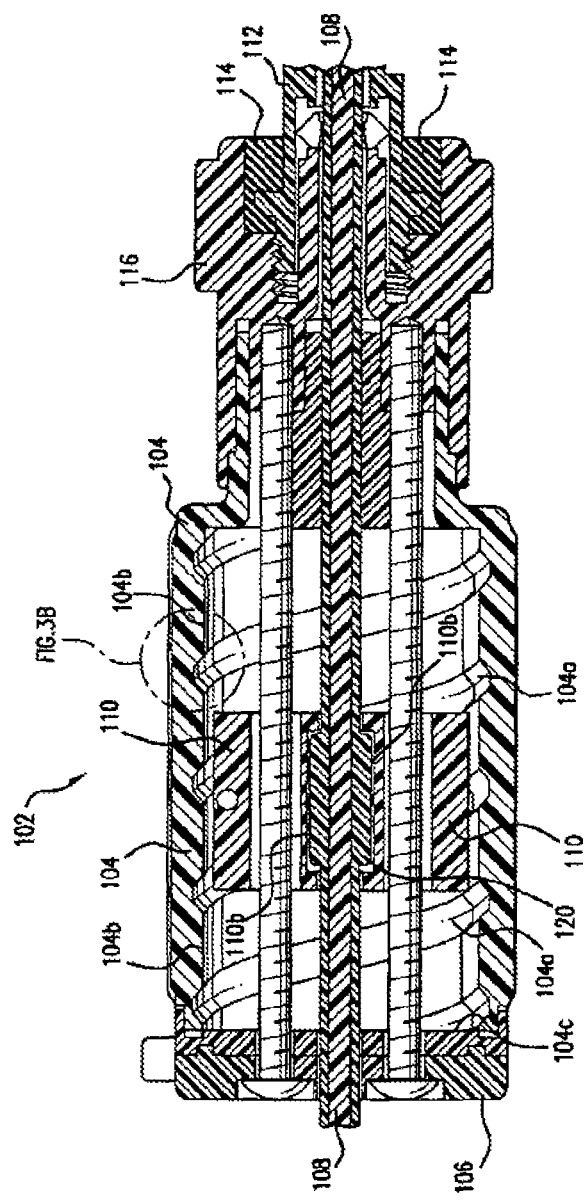
FIG. 3A shows a schematic view of the actuator handle shown with reference to FIG. 2A in accordance with one embodiment of the present invention.

FIG. 3A shows a schematic view of the actuator handle 102 shown with reference to FIG. 2A in accordance with one embodiment of the present invention. The actuator handle 102 includes a housing 104 and a bushing 110. In an embodiment of the present invention, the housing 104 maybe constructed using any high strength, durable material, such as plastic or the like. It should be noted that in an embodiment of the present invention, the housing 104 functions as a depth actuating knob (DAK) in order to control the amount of deployment of the guide tip 132 within a lumen. The housing 104 includes a groove 104a which allows travel of the bushing 110 within the housing 104 during use of the catheter device 100. As may be seen with reference to the Figure, the groove 104a is spirally disposed about an inner wall 104b of the housing 104. The groove 104a complements a bushing thread 110a disposed on the bushing 110, as shown with reference to FIG. 3B.

Figure 3B:
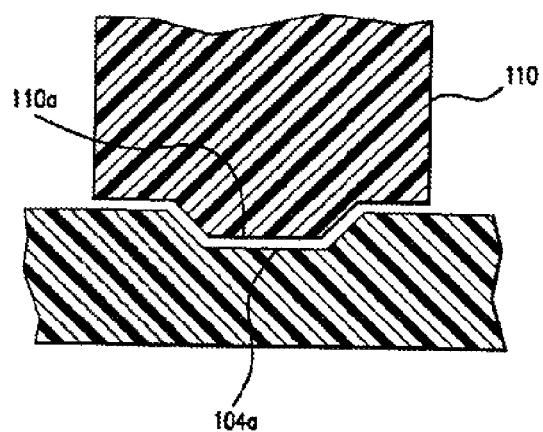
FIG. 3B illustrates a schematic view of the present invention showing a bushing thread of a bushing of the actuator handle shown with reference to FIG. 3A.

FIG. 3B is a schematic view of the present invention showing a bushing thread 110a of the bushing 110 shown with reference to FIG. 3A. The bushing thread 110a runs along a periphery of the bushing 110 such that the bushing 110 contacts the housing 104 and the groove 104a via the bushing thread 110a. As such, the bushing thread 110a allows for precise movement of the bushing 110 within the housing 104 during advancement and retraction of the guide tip 132. Therefore, when a user elects to either advance or retract the guide tip 132 within a lumen, the user moves the bushing 110 within the housing 104 via the groove 104a and the bushing thread 110a by rotating the housing 104a.

Returning attention to FIG. 3A, the actuator handle 102 also includes a rotating hemostasis valve adapter 116. The rotating hemostasis valve adapter 116 integrates the housing 104 and the inner key 108 with the rotating hemostasis valve (RHV) 112. The RHV 112 may be any rotating hemostasis valve which provides an interface between the rotating hemostasis valve adapter 116 and the inner key 108 such as a rotating hemostasis valve available from Merit Medical located in South Jordan, Utah, or the like. The RHV 112 also minimizes the possibility of buckling by the braided tube 109 during use of the catheter device 100. It should also be noted that the RHV 112 changes the direction of the nose cone 130 during operation of the catheter device 100, thereby changing the direction of the guide tip 132 and the flex guide 134. The RHV 112 may rotate 360 degrees, thereby allowing full control of the nose cone 130 and the guide tip 132.

In addition to the rotating hemostasis valve adapter 116, the actuator handle 102 also includes the inner key 108. The inner key 108 includes flanges 120 which reside within a cavity 110b of the bushing 110. In a preferred embodiment, the flanges 120 have a flush fit within the cavity 110b. Thus, when the bushing 110 advances or retracts within the housing 104, the flange 120 moves along with the bushing 10, thereby moving the inner key 108. As will be discussed in greater with reference to FIG. 6A, the braided tube 109 couples with the guide tip 132. As the bushing 110 advances the inner key 108, both the guide tip 132 and the flex guide 134 advance into the side 161b of the lumen 161, as shown with reference to FIG. 1. As such, the catheter device 100 allows precise, incremental advancement of the guide tip 132 and the flex guide 134 within the lumen 161.

The actuator handle 102 also includes a compression seal 114 which provides a seal between the inner key 108 and both the rotating hemostasis valve adapter 116 and the housing 104. The compression seal 114 provides sealing engagement between the RHV 112 and the rotating hemostasis valve adapter 116. The compression seal 114 prevents contamination of the housing 104 and the rotating hemostasis valve adapter 116 via the inner key 108.

Figure 4A:
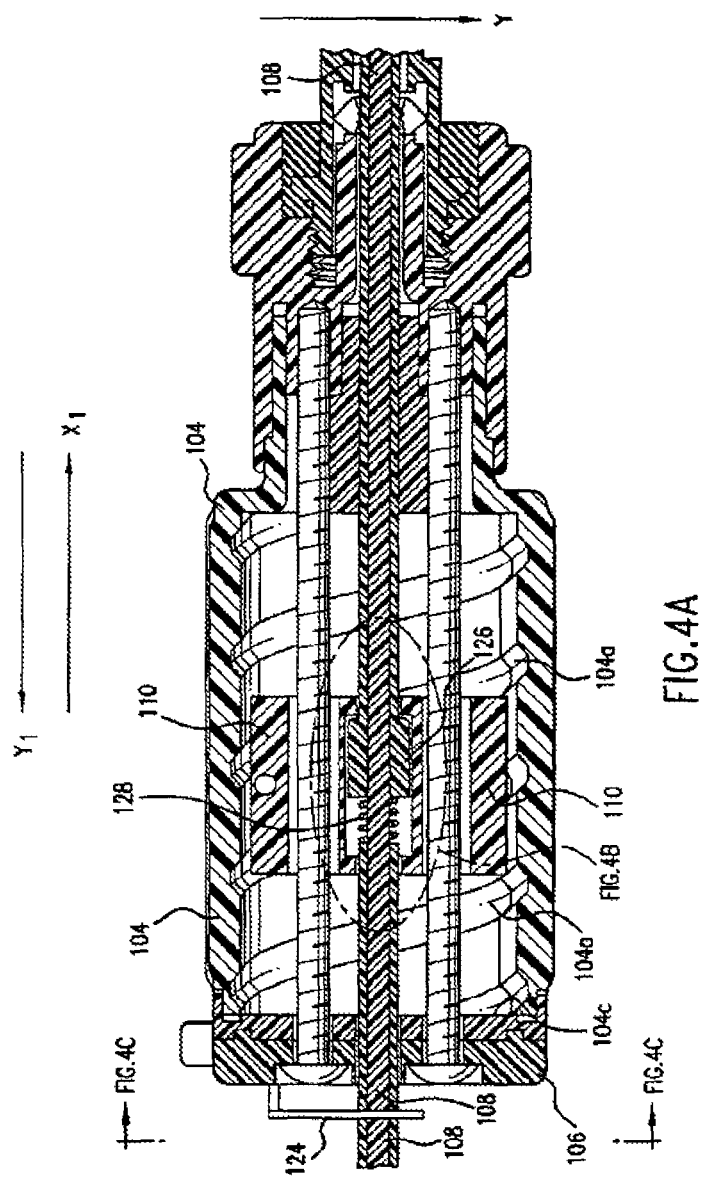
FIG. 4A shows a schematic view illustrating an alternative embodiment of the catheter device shown with reference to FIG. 2A.
Figure 4B:
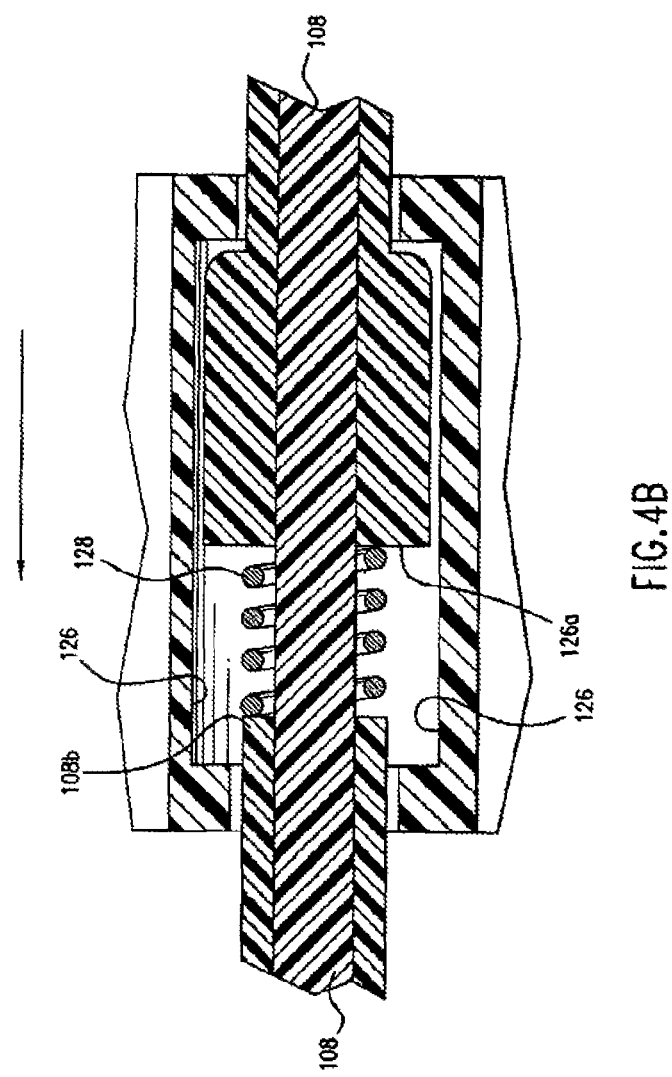
FIG. 4B illustrates a compression spring within a seat of a bushing of the catheter device shown with reference to FIG. 4A in accordance with an embodiment of the present invention.

Now making reference to FIG. 4A, FIG. 4A shows a schematic view illustrating an alternative embodiment of the catheter device 100 shown with reference to FIG. 2A. In this embodiment, the catheter device 100 includes a firing mechanism which provides automated deployment using a controlled force of the guide tip 132 within a lumen of a patient during operation of the catheter device 100. In this embodiment, the catheter device 100 includes a compression spring 128, as more clearly shown with reference to FIG. 4B. FIG. 4B illustrates the compression spring 128 within a seat 126 of the bushing 110. The compression spring 128 compresses between a surface 126a of the seat 126 and a tab 108b of the inner key 108. The compression spring 128 may be any compression spring capable of imparting a force to the flex guide 132 preferably in a range between about 0.8 lbs and about 2.5 lbs and more preferably about 2.0 lbs. As such, the catheter device 100 provides the necessary force for penetration of an arterial wall of a lumen of a patient.

Figure 4C:
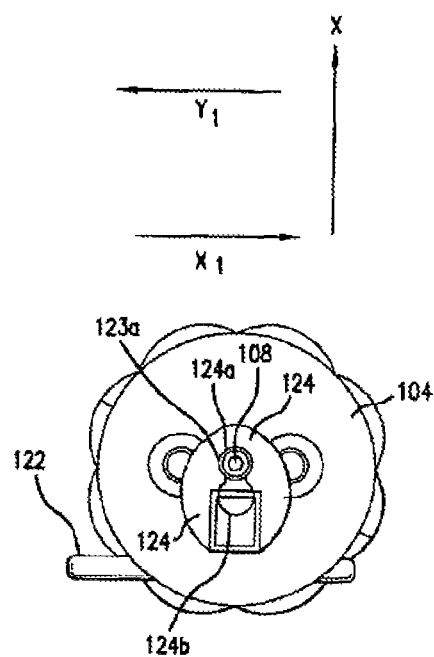
FIG. 4C is an embodiment of the present invention illustrating a front view of a firing assembly for the catheter device shown with reference to FIG. 4A.

Turning attention to FIG. 4C a firing assembly formed by a safety pin 122 and a key 124 compresses the compression spring 128 until activation by a user. The key 124 includes keyholes 124a and 124b where the keyhole 124a has a diameter smaller than a diameter of the inner key 108. Therefore, the keyhole 124a holds the inner key 108 in place prior to the deployment of the guide tip 132. The keyhole 124b has a diameter larger than the diameter of the inner key 108. Thus, upon entering the keyhole 124b, the inner key 108 advances, thereby deploying the guide tip 132 and the flex guide 134 within a lumen of a patient.

Figure 4D:
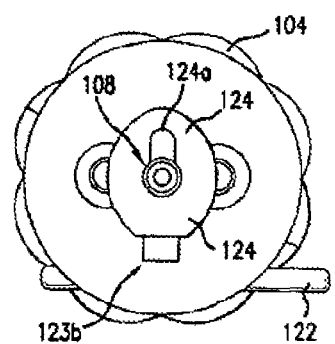
FIG. 4D is a front view of the firing mechanism shown with reference to FIG. 4C where the firing mechanism is in a fired position in accordance with an embodiment of the present invention.
Figure 4E:
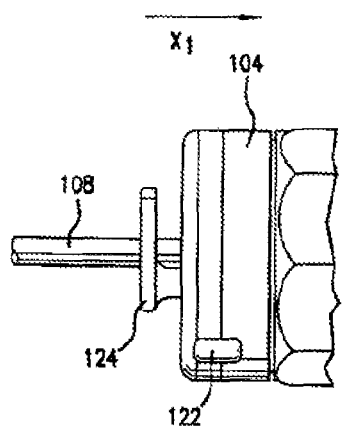
FIG. 4E is a side view of the firing mechanism shown with respect to FIG. 4D in accordance with an embodiment of the present invention.

Prior to the deployment of the guide tip 132, the inner key 108 resides within the keyhole 124a (as more clearly shown with reference to FIG. 4C) of the key 124. The safety pin 122, which includes an "L" configuration as shown with reference to the Figure, maintains the inner key 108 within the keyhole 124a during inoperation of the catheter device 100. A user engages the firing assembly by moving the safety pin 122 in a direction $X_1$ as indicated by directional arrow $X_1$. After the user moves the safety pin 122 in the direction $X_1$, the user then moves the key 124 in a direction X such that the inner key 108 moves from the key hole 124a to the key hole 124b, as shown with reference to FIG. 4D. As may be seen with respect to FIG. 4D, the keyhole 124b has a larger diameter than the inner key 108. As such, the compression spring 128 moves the inner key 108 in the direction $X_1$ (shown with reference to FIG. 4E) when the inner key 108 enters the keyhole 124b, thereby deploying the guide tip 132 through an arterial wall of a lumen of a patient.

As described with reference to the background, the motion required to deploy the guidewire from prior art catheter devices was the same as the motion used to insert the catheter device into a lumen. For example, making reference to FIG. 4A, a user inserted prior art catheter devices into a patient in the direction $X_1$. Upon insertion into the lumen, the user deployed a prior art guidewire by moving a plunger disposed at an end of the prior art catheter device in the same direction $X_1$. As may be appreciated, the user may accidentally deploy the prior art guidewire during insertion of the catheter device since the same motion was used to insert the prior art catheter device into the patient and then deploy the guidewire. The present invention avoids this problem since the user rotates the housing 104 in order to deploy the guide tip 132 within a lumen of a patient after inserting the catheter device in the direction $X_1$, as previously described.

In addition, the present invention minimizes the possibility of backing out the guide tip from the catheter device during retraction of the catheter device 100 and the guide tip 132 from the patient. As previously described, the guide tip 132 couples with the bushing 110 via the braided tube 109. The bushing 110 within the housing 104 remains fixed within the housing 104 due to the engagement between the threads 110a of the bushing 110 with the groove 104a of the housing 104. As such, as the catheter device 100 moves in the direction $Y_1$ out of the lumen of the patient, the guide tip 132 also moves in the direction $Y_1$.

Figure 5A:
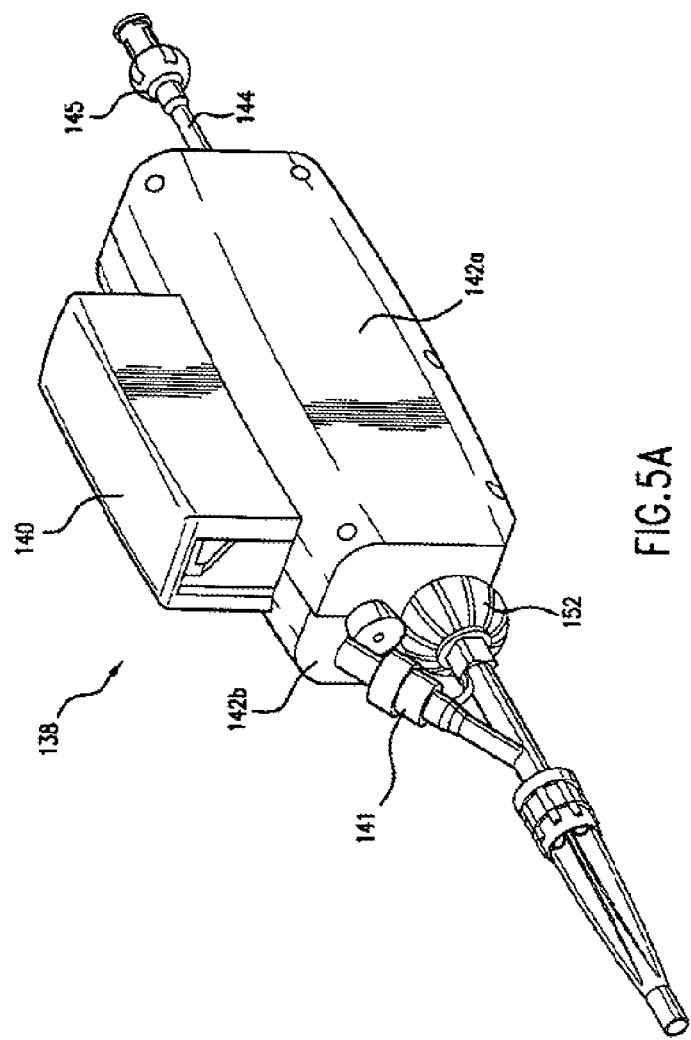
FIG. 5A illustrates a schematic view of a catheter device in accordance with an alternative embodiment of the present invention.

Now making reference to FIG. 5A, FIG. 5A illustrates a schematic view of a catheter device 138 in accordance with an alternative embodiment of the present invention. In this embodiment, the catheter device 138 includes a left handle 142a and a right handle 142b, a button 140 and a port 141. The catheter device 138 also includes an inner key 144 and a lure 145 which allows a user to lead the catheter 101 which couples with the inner key 144, during operation of the catheter device 138. As may be seen with reference to the Figure, a configuration of the left handle 142a, similar to that of the right handle 142b, allows for easy manipulation by a user as the user performs a procedure. As will be discussed in greater detail with reference to FIG. 5B, the button 140 advances the inner key 144 during operation of the catheter device 138. The inner key 144 couples with the braided shaft 109, the flex guide 134 and the guide tip 132, as previously described with reference to the inner key 108. As such, in this embodiment, the inner key 144 of the catheter device 138 includes the same functionality of the inner key 108 of the catheter device 100. In addition to the inner key 144, the catheter device 138 also includes the port 141. The port 141 allows for the addition of a fluid, such as saline solution, during operation of the catheter device 138 in order to minimize the presence of air bubbles within the catheter 101 and flush out the catheter 101 prior to use of the catheter device 100.

Now making reference to FIG. 5B, FIG. 5B is a schematic view of the catheter device 138 shown with respect to FIG. 5A without the left handle 142a in accordance with an embodiment of the present invention. The catheter device 138 also includes an actuator 146 rigidly coupled with the inner key 144 which extends from both sides of the actuator 146, as may be seen with reference to the Figure. The catheter device 138 also includes a compression spring 148 disposed coaxially about the inner key 144 between a surface 146b of the actuator 146 and a surface 150a of a rotating hub 150. During inoperation of the catheter device 138 the compression spring 148 maintains both the inner key 144 and the actuator 146 in a fixed, non-deployed position, where the button 140 is maintained in an upward position, as shown with reference to the Figure. In the embodiment of the invention shown with reference to FIG. 5B, the catheter device 138 includes the rotating hub 150 for adjusting the position of the nose cone 130. A user may use the rotating knob 150 to rotate the nose cone 130 in order to allow for precise penetration of an arterial wall of a lumen. It should be noted that in alternative embodiment of the catheter device 138, the catheter device 138 includes a rotating knob 152 as shown with respect to FIG. 5C. In this embodiment, the rotating knob 152 includes the same functionality as the rotating knob 150. Thus, a user rotates both the guide tip 132 and the flex guide 134 by rotating the rotating knob 152.

The catheter device 138 also includes the actuator 146 having gradients 146a which complement gradients 140a of the button 140. The button gradients 140a complement the actuator gradients 146a such that as a user moves the button 140 in a direction Y as indicated by directional arrow Y, the button gradients 140a slide along the actuator gradients 146a. As a user moves the button 140 in the direction Y into a configuration shown with respect to FIG. 5C, the actuator 146 moves in the direction $Y_1$. It should be noted that in this embodiment, the button 140 remains fixed with respect to the right handle 142b. Thus, when the button gradients 140a engage with the actuator gradients 146a, the engagement causes movement of the actuator 146 and the inner key 144 in the direction $Y_1$. As previously described, the inner key 144 couples with the flex guide 144 and the guide tip 132 via the braided tube 109. As such, motion of the inner key 144 in the direction $Y_1$ causes deployment of the flex guide 134 and the guide tip 132.

In addition to the actuator 146, the catheter device 138 also includes a hub assembly having a stepped hub 156, a hub stop 158 and a hub rod 159 rigidly coupled with the actuator 146. The hub assembly minimizes travel of the actuator 146 within the catheter device 138. When a user moves the button 140 in the direction Y, the button 140 continues motion until the hub stop 158, which rigidly couples with the actuator 146, contacts the stepped hub 156. When the hub stop 158 contacts the stepped hub 156, further motion of the button 140 and the guide tip 132 in the direction Y is restricted. As discussed earlier, movement of the button 140 in the direction Y controls deployment of the guide tip 132 and the flex guide 134 within a lumen. To further illustrate, the greater the button 140 moves in the direction Y, the greater deployment of the guide tip 132 and the flex guide 134 since the button 140 couples with the inner key 144. Therefore, as a result of controlling the motion of the button 140 in the direction Y, the stepped hub 156 controls the deployment of the guide tip 132 and the flex guide 134 within a lumen. The stepped hub 156 controls the amount of deployment with steps 156*a* through 156*c* as may be seen with reference to FIG. 5D.

FIG. 5D is an embodiment of the present invention illustrating a perspective view of the stepped hub 156 shown with reference to FIG. 5B. The stepped hub 156 includes the steps 156*a* through 156*c* and an actuation knob 156*d*. The hub stop 158 contacts one of the steps 156*a* through 156*c* depending upon the orientation of the stepped hub 156 within the catheter device 138. As may be seen with reference to the Figure, the steps 156*a* through 156*c* are disposed at varying depths relative to the one another. Therefore, a user controls the amount of deployment of the guide tip 132 and the flex guide 134 within a lumen via the stepped hub 156. To further illustrate, in the embodiment shown with reference to FIG. 5D, the step 156*c* is at a greater depth than the step 156*a* as indicated by a dimension Z. The step 156*c* permits greater travel of the hub stop 158 during downward motion of the button 140. Therefore, in order to increase the deployment of the guide tip 132 and the flex guide 134 within a lumen of a patient, a user rotates the actuation knob 156*d* such that the hub stop 158 contacts the step 156*c* to control deployment. Likewise, in this embodiment, a user may decrease the amount of deployment of both the guide tip 132 and the flex guide 134 by rotating the actuation knob 156*d* such that the hub stop 158 contacts either the steps 156*a* or 156*b*. It is to be understood that the hub assembly may include any number of steps which control the amount of deployment of the guide tip 132 and the flex guide 134 in addition to the steps 156*a* through 156*c* shown with respect to FIG. 5D.

Figure 5E:
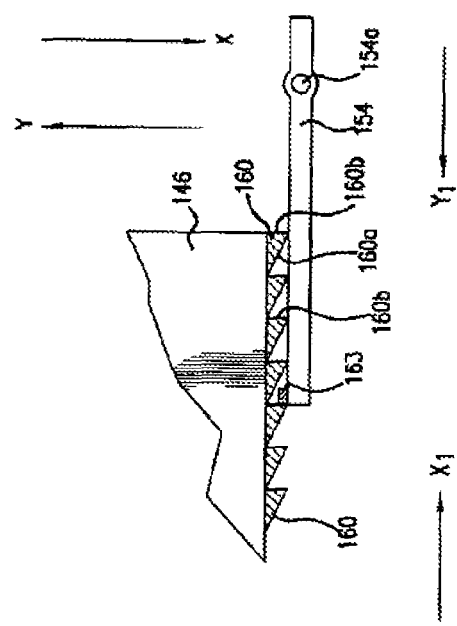
FIG. 5E is an embodiment of the present invention illustrating a method for locking a button and an actuator of the catheter device shown with respect to FIG. 5B into a position shown with respect to FIG. 5C.

During operation of the catheter device 138, the button 140 and the actuator 146 remain in the position shown with respect to FIG. 5C with a ratchet assembly shown with reference to FIG. 5E. FIG. 5E shows an embodiment of the present invention illustrating a method for locking the button 140 and the actuator 146 into the position shown with reference to FIG. 5C. The actuator 146 includes ratchets 160 having a gradient 160*a* and a surface 160*b* which engage a stop 163 of a lock 154. As previously mentioned, during operation of the catheter device 138, a user moves the button 140 in the downward direction X. When the user moves the button 140 in the downward direction X, the actuator 146 moves in the direction $Y_1$. As the actuator 146 moves in the direction $Y_1$, surfaces 160*a* of the ratchets 160 slide over the stop 163. The surfaces 160*a* continue sliding over the stop 163 until the hub stop 158 engages with the hub assembly of the catheter device 138, as described earlier. Upon engagement of the hub stop 158 with the hub assembly, the stop 163 engages with a surface 160*b* of the ratchets 160, thereby preventing movement of the actuator 146 in the direction $X_1$ and locking the position of the guide tip 132 and the flex guide 134 within a lumen of a patient. The lock 154 includes a compression spring 154*b* (more clearly shown with reference to FIG. 5B) which imparts a force in the direction Y, thereby maintaining engagement between the lock 154 and the actuator 146. Once the user completes a procedure using the catheter device 138, the user disengages the lock 154 by rotating the lock 154 about pivot 154*a* in a direction $Y_2$, as indicated by directional arrow $Y_2$, which allows motion of the actuator 146 in the direction $X_1$.

Now making reference to FIG. 6A, FIG. 6A is a schematic view of the nose cone 130 shown with reference to FIG. 1 in accordance with an embodiment of the present invention. The nose cone 130 houses both the guide tip 132 and the flex guide 134 prior to deployment of the guide tip 132 and the flex guide 134 within a lumen. The nose cone 130 includes a lumen (not shown) which allows back loading of the catheter 101 over a guidewire. In an embodiment of the present invention, the lumen may be sized to accept a guidewire. Guidewires are provided in many diameters, such as 0.018 inch or 0.035 inch, for instance. In a preferred embodiment, the lumen is sized to accept a 0.035 inch guidewire. It should also be noted that in this embodiment of the present invention, the nose cone 130, along with the guide tip 132 and the flex guide 134, may be radiopaque for visualization under a fluoroscope.

The nose cone 130 includes cam surfaces 130*a* through 130*c* which pivot the guide tip 132 as the guide tip 132 deploys from the nose cone 130. In accordance with an embodiment of the present invention, the nose cone cam surfaces 130*a* may be formed at an angle H in a range preferably between about 20 degrees and about 50 degrees and more preferably about 30 degrees. The guide tip 132 includes a cam surface 132*a*, a curved portion 132*b* and a tip 132*d*. The guide tip cam surface 132*a* engages with the nose cone cam surfaces 130*a* through 130*c* during deployment of the guide tip 132 from the nose cone 130. As previously discussed, when either the inner key 108 or the inner key 144 are engaged by a user, both the inner key 108 and the inner key 144 move the flex guide 134 and the guide tip 132 in a direction $Y_1$. As the guide tip 132 moves in the direction $Y_1$, the nose cone cam surface 132*a* first contacts the guide tip cam surface 130*a* such that the nose cone cam surface 130*a* moves the guide tip 132 in a direction $X_2$ as indicated by directional arrow $X_2$. The guide tip cam surface 132*a* then contacts the nose cone cam surface 130*b*, which further rotates the guide tip 132 in the direction $X_2$. Upon engagement with the guide tip cam surface 130*b*, the guide tip cam surface 132*a* then engages the nose cone cam surface 130*a*, which further rotates the guide tip 132 in the direction $X_2$ and orientates the guide tip 132 as shown with respect to FIG. 6B. It should be noted that the flex guide 134 follows the same path as the guide tip 132 such that the flex guide 134 also deploys from the nose cone 130 as shown with respect to FIG. 6B.

During operation of the catheter devices 100 and 138, the tip 132*d* penetrates a lumen of a patient thereby allowing passage of the flex guide 134 into the lumen upon penetration. In an embodiment of the present invention, the guide tip 132 may be constructed from platinum iridium, stainless steel or any material being radiopaque and having high strength properties having a high resisitivity to bending. In addition, the guide tip 132 may be a needle capable of penetrating of an arterial wall of a lumen.

Figure 6C:
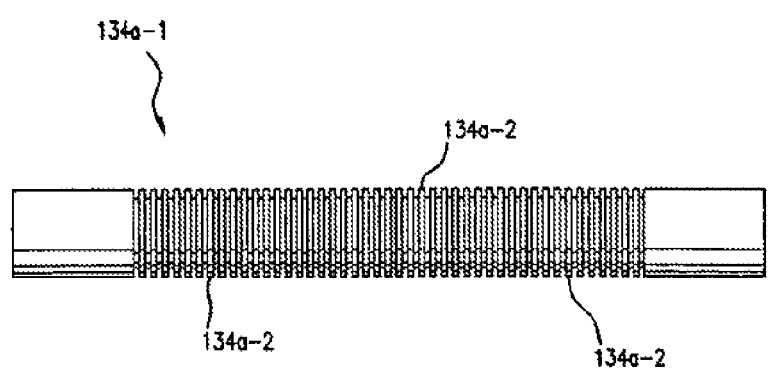
FIG. 6C illustrates a schematic view of an alternative embodiment of a flex guide in accordance with an embodiment of the present invention.

In an embodiment of the present invention, the flex guide 134 may also be constructed from stainless steel or any similar material having high strength properties. The flex guide 134 also includes cut-outs 134*a* disposed throughout the flex guide 134 which increase the flexibility of the flex guide 134. The cut-outs 134*a* are configured to control column strength of the flex guide 134 and allow flexing of the flex guide 134 as the flex guide 134 deploys from the nose cone 130 and enters a lumen of a patient. In one embodiment of the present invention, the cut-outs 134a may have a multiple slot configuration as shown with reference to FIG. 6B. It should be noted that the slots of cut-outs 134a may have any configuration (i.e., E configuration, etc.) which allows both control of column strength and flexing. In accordance with an alternative embodiment of the present invention, the flex guide 134 may also have the configuration shown with reference to FIG. 6C. In this embodiment, a flex guide 134a-1 has a bellows configuration where the flex guide includes a plurality of bellows 134a-2 which allow flexing of the flew guide 134a-1 during deployment of the guide tip 132. In addition, the bellows configuration of the flex guide 134a-1 allows control of column strength.

The slots may be formed in the flex guide 134 using any suitable technique for forming cut-outs in a high strength material, such as laser cutting, electrical discharge machining, stamping or the like. In this embodiment, the cut-outs 134a are continuously formed within the flex guide 134. Moreover, the cut-outs 134a are formed 90 degrees relative to one another as more clearly shown with reference to FIG. 6B, thereby further increasing overall flexibility and column strength of the flex guide 134.

Figure 6D:
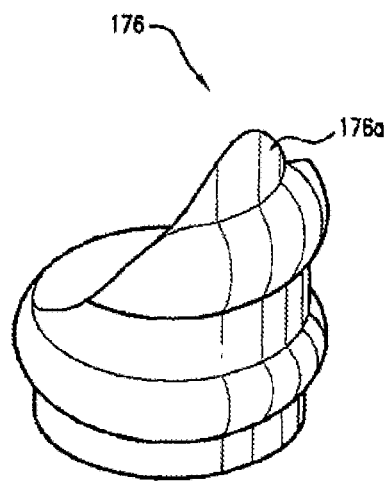
FIG. 6D shows a perspective of an alternative embodiment for the catheter device shown with reference to FIGS. 2A and 5A.

In accordance with an alternative embodiment of the present invention, the catheter devices 100 and 138 may also have a guide tip 176 as shown with reference to FIG. 6D. In this embodiment, the guide tip 176 has a circular configuration and a tip 176a which penetrates an arterial wall of a lumen during operation of the catheter devices 100 and 138. In addition, the configuration of the tip 176a minimizes the possibility of improper penetration by the guide tip 176 during penetration of an arterial wall.

Figure 6E:
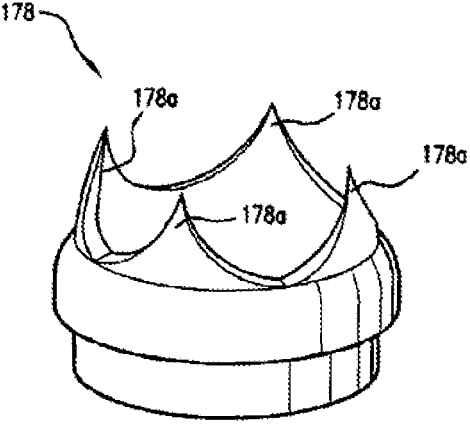
FIG. 6E illustrates a perspective view of a guide tip which includes a plurality of tips in accordance with an embodiment of the present invention.

A guide tip for the catheters 100 and 138 may also have the configuration shown with respect to FIG. 6E. FIG. 6E illustrates a perspective view of a guide tip 178 which includes a plurality of tips 178a in accordance with an embodiment of the present invention. In this embodiment, the plurality of tips 178a have a circumferential configuration about a periphery of the guide tip 178. The circumferential configuration allows proper penetration of an arterial wall of a lumen regardless of the orientation of the guide tip 178 relative to the arterial wall. Thus, the circumferential configuration of the tips 178a improves reliability and decreases overall costs associated with a catheter device implementing the guide tip 178.

The catheter devices 100 and 138 may also be configured for anchoring within the subintimal space during operation of the catheter device 100, as shown with reference to FIG. 7. In this embodiment, during operation of either the catheter device 100 or 138, a user deploys a balloon 168 of the catheter device 100 which anchors the catheter device 100 during deployment of the guide tip 132 and the flex guide 134. In this embodiment, the balloon 168 may be any balloon suitable for anchoring the catheter device 100 within a subintimal space of a lumen, such as a polytetrafluoroethylene (PTFE) balloon. Upon anchoring within the subintimal space, a user deploys the guide tip 132 and the flex guide 134.

Figure 8A:
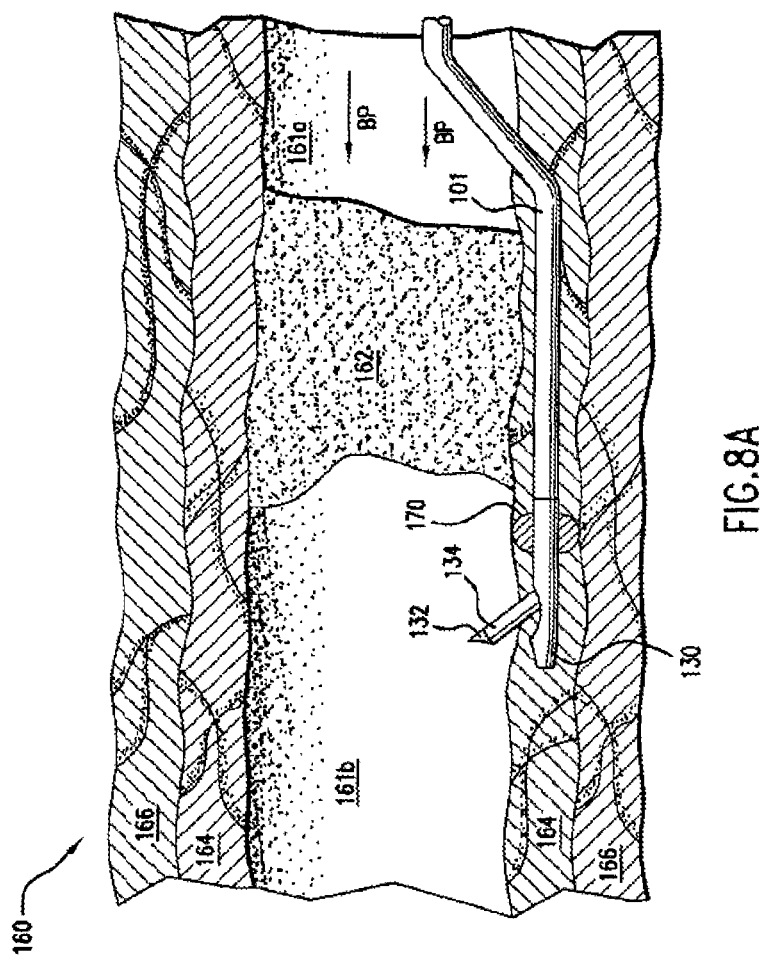
FIG. 8A shows a schematic view of the catheter device shown with reference to FIG. 2A where the catheter device includes anchors for anchoring a guide tip within a subintimal space of a lumen in accordance with an embodiment of the present invention.
Figure 8B:
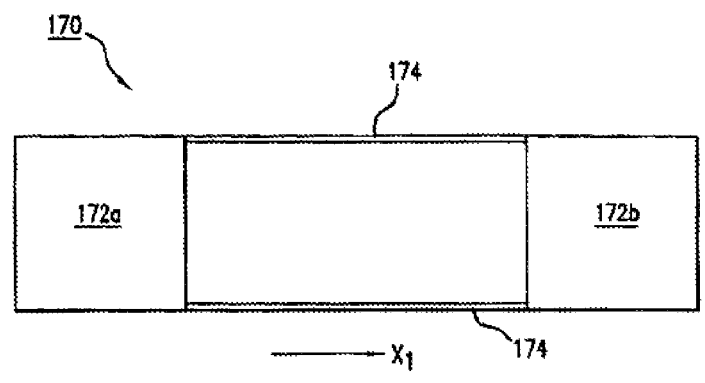
FIG. 8B illustrates a schematic view of spacers and anchors disposed within the catheter device shown with reference to FIG. 8A in accordance with an embodiment of the present invention.
Figure 8C:
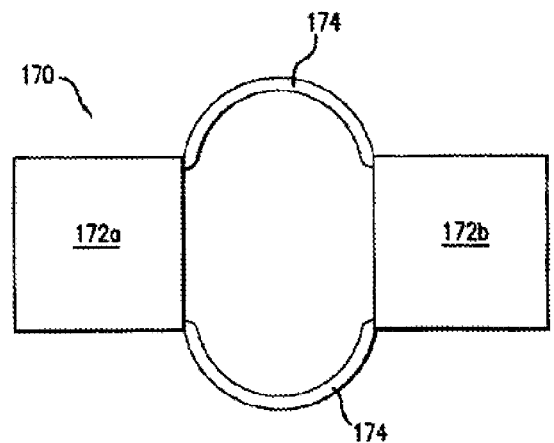
FIG. 8C shows a schematic view of the spacers and the anchors shown with respect to FIG. 8B in a deployed position in accordance with an embodiment of the present invention.

In addition to the balloon 168, the catheter device 100 may also include an anchoring assembly 170 shown with reference to FIG. 8A. In this embodiment, the anchoring assembly includes spacers 172a and 172b and anchors 174 as shown with respect to FIG. 8B. The anchors 174 may be constructed of any material capable of bowing, such as nylon, silicon, C-flex® or the like. Once a user properly orientates the catheter device 100 within the subintimal space of the lumen 160, the user anchors the catheter device 100 with the anchoring assembly 170. The user anchors the catheter device 100 by moving the spacer 172a in the direction $X_1$. As the spacers 172a and 172b move, the anchors 174 flex as shown with respect to FIG. 8C. Once the anchors 174 flex, the catheter device 100 has the orientation shown with reference to FIG. 8A. It should be noted that the catheter device 138 may also employ the anchoring assembly 170 for anchoring within the subintimal space of a lumen of a patient. After deployment of the guide tip 132 and the flex guide 134 within a lumen a patient, a catheter may be fed over both the guide tip 132 and the flex guide 134 in order to allow blood passage around the occlusion 162.

The present invention now offers physicians performing vascular intervention an attractive alternative to direct guidewire around an occlusion within a lumen ultimately resulting in recanelization of a lumen. The present invention provides surgeons with an automated method for incrementally and accurately deploying a guide tip within the patient of a lumen with precision. Moreover, the present invention provides a hard stop during needle deployment, thereby avoiding the prior art problem of puncturing an arterial wall. Thus, the surgeon saves the time required to accurately and precisely perform a peripheral vascular intervention procedure, thereby decreasing the overall time a patient spends in surgery and decreasing the overall costs associated with spending time in surgery.

The above are exemplary modes of carrying out the invention and are not intended to be limiting. It will be apparent to those of ordinary skill in the art that modifications thereto can be made without departure from the spirit and scope of the invention as set forth in the following claims.

What is claimed is:

1. A catheter device comprising:
   a housing;
   a shaft adaptor connected to the housing, the shaft adaptor comprising a rotatable guide having one or more interfaces;
   an inner key extending distally from the shaft adapter, the inner key having one or more interfaces that engage the one or more interfaces of the shaft adaptor; and
   a nose cone connected to a distal end of the inner key, the inner key connecting the nose cone and the housing, the nose cone comprising a guide tip, the nose cone being configured to rotate when the guide rotates.

2. The catheter device of claim 1, wherein the inner key comprises a braided tube.

3. The catheter device of claim 2, wherein the inner key is configured to rotate when the guide rotates.

4. The catheter device of claim 2, further comprising a rotatable knob operatively associated with the housing and the inner key.

5. The catheter device of claim 4, wherein the nose cone is configured to rotate with the rotatable knob.

6. The catheter device of claim 2, wherein the nose cone houses a flex guide having one or more cuts to control the flexibility or column strength of the flex guide.

7. The catheter device of claim 2, wherein the nose cone houses a flex guide having one or more bellows to control the flexibility or column strength of the flex guide.

8. A catheter device comprising:
   a housing;
   an inner key extending distally from the housing;
   a rotatable knob operatively associated with the housing and the inner key; and
   a nose cone connected to a distal end of the inner key, the inner key connecting the nose cone and the housing, the nose cone comprising a guide tip, the nose cone being configured to rotate when the rotatable knob rotates.

9. The catheter device of claim 8, wherein the nose cone houses a flex guide having one or more cuts to control the flexibility or column strength of the flex guide.

10. The catheter device of claim 8, wherein the nose cone houses a flex guide having one or more bellows to control the flexibility or column strength of the flex guide.

11. The catheter device of claim 8, the nose cone including a nose cone cam surface and the guide tip comprising a guide tip cam surface, the nose cone cam surface configured to engage with the guide tip cam surface.

12. The catheter device of claim 8, wherein the guide tip includes at least one tip configured to penetrate body tissue.

13. The catheter device of claim 12, wherein the guide tip includes a plurality of circumferentially spaced apart tips disposed about a periphery of the guide tip.

14. A catheter device comprising:
a housing;
an inner key extending distally from the housing; and
a nose cone connected to a distal end of the inner key, the nose cone comprising a flex guide having one or more cut-outs or one or more bellows to control the flexibility or column strength of the flex guide.

15. The catheter device of claim 14, wherein the one or more cuts are continuously formed within the flex guide.

16. The guide device of claim 14, wherein the one or more bellows are spaced longitudinally along the flex guide.

17. The guide device of claim 14, further comprising an anchoring member disposed about a braided tube coupled to the inner key.

18. The guide device of claim 17, wherein the anchoring member is a balloon mounted to the nose cone.

19. A method for advancing a guide tip through an arterial wall defining a lumen using a catheter device, the catheter device including a housing with an actuator movably disposed therein and a button associated with the actuator, the method comprising:
introducing a catheter having an inner key within a lumen of a patient on a first side of an occlusion within the lumen, wherein the inner key couples with the actuator;
navigating around the occlusion within the lumen to a second side of the occlusion with the catheter; and
advancing the guide tip through the arterial wall and into the lumen on the second side of the occlusion by moving the button in a first direction relative to the housing, the inner key being configured to move in a section direction upon movement of the button in the first direction, thereby advancing the guide tip.

20. The method as recited in claim 19, wherein moving the button engages one or more button gradients associated with the button with one or more actuator gradients associated with the actuator.

21. The method as recited in claim 20, wherein the catheter includes a first handle and a second handle, the button remaining fixed with respect to the first handle.

22. The method as recited in claim 21, wherein moving the button in the first direction comprises moving the button in a direction transverse to a longitudinal axis of the actuator.

23. The method as recited in claim 22, further comprising anchoring the catheter within tissue.

24. The method as recited in claim 23, wherein anchoring the catheter within tissue comprises deploying an anchor of an anchoring assembly, the anchor comprising a material capable of bowing.

* * * * *